United States Patent [19]

Gierhart

[11] Patent Number: 5,308,759

[45] Date of Patent: May 3, 1994

[54] PRODUCTION OF ZEAXANTHIN AND ZEAXANTHIN-CONTAINING COMPOSITIONS

[75] Inventor: Dennis L. Gierhart, High Ridge, Mo.

[73] Assignee: Applied Food Biotechnology, Inc., Fenton, Mo.

[21] Appl. No.: 841,193

[22] Filed: Feb. 21, 1992

Related U.S. Application Data

[63] Continuation of Ser. No. 400,396, Aug. 30, 1989, abandoned.

[51] Int. Cl.⁵ .......................... C12P 23/00; C12N 1/20
[52] U.S. Cl. ........................................ 435/67; 435/850; 435/252.1; 424/93 D; 426/61; 426/250
[58] Field of Search .................... 435/67, 850, 252.1, 435/195; 424/93 D; 426/61, 250

[56] References Cited

U.S. PATENT DOCUMENTS

| | | | |
|---|---|---|---|
| 2,515,135 | 7/1950 | Petty | 99/9 |
| 2,974,044 | 3/1961 | Farrow et al. | 99/4 |
| 3,841,967 | 10/1974 | Dasek et al. | 435/67 |
| 3,891,504 | 6/1975 | Schocher et al. | 435/67 |
| 3,920,834 | 11/1975 | Klaui et al. | 424/305 |
| 3,951,742 | 4/1976 | Shepherd et al. | 435/67 |
| 3,951,743 | 4/1976 | Shepherd et al. | 435/67 |
| 4,001,084 | 1/1977 | Horwath et al. | 435/252.1 |
| 4,026,949 | 5/1977 | Boguth et al. | 260/606.5 |
| 4,039,384 | 8/1977 | Suzuki et al. | 435/252.1 |
| 4,642,131 | 2/1987 | Hoitink | 71/6 |
| 4,713,340 | 12/1987 | Crawford | 435/253 |

OTHER PUBLICATIONS

"Carotenoids", Microbial Technology, Chapter 17, 2d ed., vol. 1, 1979.
Hanson, "Microbial Production of Pigments and Vitamins", Chapter 10, 1st ed., 1967, pp. 222–247.
ATCC Catalogue of Bacteria, 1992, p. 293.
McDermott et al., *S. of Gen. Microbiol*, 1973, vol. 77, pp. 161–171.
Britton et al., *Arch Microbiol.*, vol. 113, pp. 33–37, 1977.
Johnson et al. *Aquaculture,* vol. 20, pp. 123–134, 1980.
Stanbury et al., "Principles of Fermentation Technology", 1984, pp. 77–82, Pergamon Press.
Holmes et al., *Int. J. of Syst. Bacteriol.*, vol. 31, pp. 21–34, 1981.

*Primary Examiner*—Irene Marx
*Attorney, Agent, or Firm*—Leydig, Voit & Mayer, Ltd.

[57] ABSTRACT

Zeaxanthin is produced using *Flavobacterium multivorum*. The process and the nutrient medium used in the process provide greater zeaxanthin and cell yields per liter, at a lower cost, and more rapidly than known methods and microorganisms. Biomass compositions containing the microorganism of this invention are also disclosed.

19 Claims, No Drawings

PRODUCTION OF ZEAXANTHIN AND ZEAXANTHIN-CONTAINING COMPOSITIONS

This is a continuation of copending application Ser. No. 07/400,396 filed on Aug. 30, 1989, now abandoned.

The present invention involves the production of zeaxanthin using a microorganism of the species *Flavobacterium multivorum*, nutrient media for culturing and fermenting *F. multivorum*, compositions that include *F. multivorum* cell particles, and compositions that include zeaxanthin produced by a microorganism of this invention.

BACKGROUND AND SUMMARY OF THE INVENTION

Zeaxanthin (3,3'-dihydroxy-$\beta$-carotene) is a carotenoid that imparts the yellow color to corn, egg yolks and the skin of poultry. It can be used as a feed additive and as a colorant in the cosmetic and food industries.

The pure zeaxanthin and the pigment-containing cell-mass manufactured according to the process of this invention can be used for the coloring of foodstuffs, as well as for the coloring of cosmetic preparations. The pigment-containing cell-mass is particularly suitable for the coloring of legs, beaks, skin, fat, flesh and egg-yolk of poultry.

Zeaxanthin is synthesized biologically by very few bacterial species of the genus Flavobacterium. With rare exceptions, all Flavobacterium species may be conveniently placed into two categories: 1) strongly proteolytic (digestion of gelatin, casein, and coagulated serum), and 2) nonproteolytic. *F. meningosepticum* (biovar IIa) and *F. indologenes* (viovar IIb) are always proteolytic; other flavobacteria are not (IIc, IIe, IIh, IIi, and IIk-2). *F. multivorum* is one of three species now recognized in CDC's IIk-2 group (non-proteolytic).

For poultry producers, there has been a long history of problems with stability and biological availability, particularly with xanthophylls from marigolds and alfalfa. Much work goes on to measure and improve these properties. Most marigold products must be solvent-extracted and saponified, and may require the inclusion of antioxidants in the extraction process (Marusich and Bauerfeind, *Carotenoids As Colorants and Vitamin A Precursors;* ed., J. C. Bauerfeind, Academic Press, 1981). The feeding studies shown in Example 6 directly compared a known amount of pigment versus several processed extracts from marigolds; the data indicate that the composition of the present invention is biologically available and stable, pigments faster, and is 2–3 times more potent, on a pure pigment basis, than marigold xanthophylls.

It is known that several species of Flavobacterium, under certain process conditions and/or using certain nutrient media, are capable of producing zeaxanthin (see the Relevant Literature section).

It is also known that improved yields of zeaxanthin may be obtained by culturing a microorganism of the genus Flavobacterium under conditions whereby the amounts of carbon and nitrogen present in the culture medium are maintained at a substantially constant ratio. The nutrient media of these processes require glucose and other nutrients, which are relatively costly and require a long culturing period.

On the other hand, the present invention provides a process for preparing zeaxanthin by culturing a zeaxanthin-producing microorganism of *Flavobacterium multivorum*, the first time that this species of Flavobacterium has been shown to produce pigment. Moreover, the nutrient medium in which the microorganism is cultured is a relatively low cost nutrient medium. Furthermore, the culturing period is much faster and more efficient than known methods.

Accordingly, an object of the present invention is to provide a process for the preparation of zeaxanthin using a strain of *Flavobacterium multivivorum*, or a mutant or variant thereof. The process according to the present invention makes it possible to obtain increased amounts of zeaxanthin and increased cell yields of zeaxanthin-containing cells in comparison to known microorganisms and processes.

It is another object to provide a process for producing increased yields of the biologically available zeaxanthin pigment.

It is another object to provide a process for producing zeaxanthin using microorganisms that are non-fastidious, grow rapidly, and are non-pathogenic. These microorganisms are also capable of using a nutrient medium containing many different carbon sources.

It is another object to provide an economical and commercially feasible nutrient medium, which optimizes the amount of zeaxanthin produced, provides a high cell yield, provides a high yield of zeaxanthin, and decreases the fermentation period for producing zeaxanthin.

Another object is to provide a bacterial species that produces zeaxanthin.

Another object is to provide a microorganism heretofore not known to produce zeaxanthin.

These objects and others will become apparent in the following description of the invention and in the claims.

RELEVANT LITERATURE

U.S. Pat. No. 3,891,504 discloses compositions and a method for producing zeaxanthin. The two Flavobacterium species are identified as ATCC Nos. 21588 and 21081. These strains were fermented in a nutrient medium, which included glucose, tryptone and a yeast extract, and were subjected to a process that included temperature shifts and the use of pigment promoters (lactic acid and palmitic acid methylesters).

U.S. Pat. Nos. 3,841,967; 3,951,742; and 3,951,743 disclose the use of Flavobacterium strains (identified as ATCC Nos. 21588, 21081 and 11947) in a process for producing zeaxanthin using a method similar to that for $\beta$ carotene production. The process involves the growth of the microorganism in a batch-feed glucose nutrient medium, with the exception that the culture is continuously fed additional nutrients to maintain a constant carbon/nitrogen ratio. These patents also disclose a mutation procedure for isolating high pigment-producing bacterial strains. The process using this mutant produces high levels of zeaxanthin, but it is not economical.

U.S. Pat. No. 4,026,949 discloses the production of optically active intermediates used in the production of carotenoid, such as zeaxanthin; the bacteria used in this process is *Flavobacterium dehydrogenans*.

SPECIFIC DESCRIPTION OF THE INVENTION

The present invention involves the production of zeaxanthin using a microorganism, *Flavobacterium multivivorum*, not heretofore known to produce this pigment. The invention involves isolating *Flavobacterium multivivorum* cells and culturing them in a nutrient medium under conditions in which zeaxanthin is produced in recoverable amounts. The microbial cells can be separated from the fermentation liquor and used in biomass compositions.

Accordingly, the present invention is a process for producing zeaxanthin using *Flavobacterium multivorum*, compositions that include *Flavobacterium multivorum* cells or cell particles, and compositions that include zeaxanthin produced by *Flavobacterium multivorum*.

The term "*Flavobacterium multivorum*" is intended to include all microorganisms of the genus *Flavobacterium* and species *multivorum* that produce zeaxanthin, including their subcultures (mutants and variants), which cannot be definitely differentiated from the bacterial strain(s) described in the Examples or in Bergey's Manual (1984 Edition). Characteristics of *F. multivorum* are provided below, and a taxonomic description of *F. multivorum* strain AFB-44, ATCC 552138, is provided in Example 4. The term "mutants" as used herein includes mutants produced from *Flavobacterium multivorum* by various means, including but not limited to chemical mutagenic agents, ultraviolet radiation, phage exposure and the like. These processes and agents are well-known to practitioners in the art. Mutants described in this patent application were subjected to standard mutagenesis by NTG (n-methyl-N-nitro N-nitrosoguanidine) and to ultraviolet radiation, as described in *Manual of Methods for General Bacteriology*; ASM 1981, Chapter 13. The term "variants" as used herein includes variants of *Flavobacterium multivorum*, including but not limited to those described in Bergey's Manual (1984 Edition). The term "biomass" is used herein to include non-viable, zeaxanthin-containing *Flavobacterium multivorum* cells, residual debris, including unused media solids, recovered from fermentation of live *Flavobacterium multivorum* cells, and powders derived from this material. Said biomass may also include certain well-known additives, antioxidants, chelating agents, and emulsifiers and stabilized powders derived from this material. The biomass may be placed in an inert carrier containing, for example, starch and/or residual fermentation powder and/or one or more flours.

*Flavobacterium multivorum* grow in smooth, nonpigmented colonies of less than 1 mm on a 1-day sheep blood agar plate; the plate shows no zones of inhibition surrounding penicillin, vancomycin, and polymyxin disks. The microorganisms are strongly oxidase-positive, catalase-positive, gram negative rods; non-motile; strongly sucrose-positive (most non-fermenting bacteria are sucrose-negative); always mannitol-negative and ethanol-negative; and urea-positive.

Producing zeaxanthin according to the present invention can be conducted using conventional culturing techniques well-known to practitioners in the art of producing zeaxanthin. See, for example, U.S. Pat. Nos. 3,891,504; 3,841,967; 3,951,742; and 3,951,743. Briefly, *Flavobacterium multivorum* cells may be isolated in a known manner, the yellow cultures may be purified and subjected to cultivation on solid nutrient media or in liquid nutrient solutions under conditions in which zeaxanthin is produced intracellularly. The cell may be extracted with an organic solvent, and the zeaxanthin analyzed using spectrophotometry and high pressure liquid chromatography (HPLC).

However, according to the present invention, the preferred process for producing zeaxanthin is shown in Example 2.

Preferably, the isolation and pure cultivation of the yellow Flavobacterium microorganisms of this invention are effected as follows. Material from a spring or other natural source, used as the source of the microorganisms, is suspended in physiological saline. Streak cultures are applied to Petri dishes. Then, the yellow colonies growing on the agar are examined for carotenoid content. Colonies of *Flavobacterium multivorum* can be identified by comparing the cells to the taxonomic description provided in Bergey's Manual (1984 edition). Finally, the *Flavobacterium multivorum* microorganisms of this invention are identified by their zeaxanthin content [confirmed by analytical procedures, preferably high performance liquid chromatography; F. Quackenbush, *J. Liquid Chromatography*, 10(4) pp. 643–653 (1987)] and isolated. Methods of determining zeaxanthin-producing microorganisms include but are not limited to high performance liquid chromatography. Other processes for isolating *F. Multivorum* are known to practitioners in the art, and are suitable for use in this invention. Strains of *F. multivorum* are also available through the American Type Culture Collection and various public and private depositories throughout the world.

The microorganisms employed in the present process can be cultivated in a nutrient medium in a conventional manner. In cultivating the microorganisms, many conventional solid nutrient media (or any conventional liquid nutrient solution media) that contain assimilable carbon or nitrogen can be utilized. The term "nutrient medium" designates a culture medium containing assimilable substances necessary for the growth of the microorganism. These substances include, in particular, a source of readily assimilable carbon and a source of readily assimilable nitrogen, and mineral salts, as noted below. The nutrient medium may also contain optional additives, such as vitamins, pigment formation promoters, growth factors, certain inorganic salts, such as NaCl (which are conventionally present in such media), and trace elements, as noted below.

However, according to the present invention, the preferred medium has the following composition (percentages are by weight of total medium):

| | |
|---|---|
| Nitrogen source | 3–10% |
| Carbon source | 1–7% |
| Minerals | .0001–0.5% |
| Na$_2$HPO$_4$ | 0–1% |
| Fat source | .5–3% |
| Growth factor(s) | 0–1% |
| Enzyme | .001–.1% |
| Water | remainder |

Sources of readily assimilable nitrogen include but are not limited to numerous substances of animal, vegetable and/or microbial origin as well as inorganic nitrogen compounds. Among the preferred sources of readily assimilable nitrogen are soya meal, fish meal, meat meal, meat extract, peptone, corn steep liquor, yeast extract, amino acids, ammonium salts (such as ammonium phosphate or ammonium sulfate), and protein hydrolysates, in particular products obtained by the acidic or enzymatic hydrolysis of vegetable proteins, such as soybeans, soya, or peanut proteins and/or the casein hydrolysate called tryptone. The nitrogen source may also contain a material prepared by acidic or enzymatic hydrolysis of a biomass recovered as a byproduct in the biosynthesis of a carotenoid pigment by culture of a bacterium of the Flavobacterium genus, in particular by the hydrolysis of a biomass of Flavobacterium cultured for the production of zeaxanthin and from which the pigment has been extracted.

The most preferred assimilable nitrogen source is corn steep liquor, because of its low cost and the presence of desirable growth factors.

Sources of readily assimilable carbon include but are not limited to sugars and their polymers, such as starches, dextrin, saccharose, maltose, lactose, glucose, and molasses; fatty acids; and polyalcohols, such as glycerine. Preferred carbon sources include corn, corn flour, rice, milo, wheat, starch, lactate, acetate, and gluclose feed. The glucose level in the media is less than about 0.035% by weight. Corn flour is most preferred because of its price, particle size, and culture use at levels ranging from 1–7% by weight of the total medium. As is evident to one skilled in the art, corn, corn flower, and starch require treatment with a starch liquefaction enzyme, such as α-amylase (commercially available as Termamyl 120L), which hydrolyzes starch to dextrin. Without this treatment, the starch would set up into a solid mass upon heating. However, too much enzymatic hydrolysis reduces yields, while too little hydrolysis reduces yields and increases fermentation times.

The nutrient media may also contain trace elements originating from present or added mineral or organic ingredients. For example, sulphur and phosphorus can originate from inorganic or organic ingredients present in the nutrient medium, or they can be specifically added to the nutrient medium. If desired or required, growth-promoting agents or stimulants such as, for example, vitamins, can also be added to the nutrient medium. The preferred minerals are low levels of ferrous sulfate (which improves cell growth) and disodium phosphate.

The fat source includes but is not limited to soapstock, soybean oil, sunflower oil, and olive oil; soapstock is preferred.

Cultivation is preferably carried out by employing certain growth factors or yield-promoting additives in the media. The preferred growth factor is yeast extract.

The strains utilizable for the cultivation process can be introduced to the fermenting vessel from the streak culture plate according to known methods. The preferred methods are via the agar-slant culture and glass-flask liquid culture.

Cultivation of the microorganism under conditions that lead to the formation of zeaxanthin, according to the process of this invention, may be carried out in any conventional manner. In accordance with a preferred embodiment of carrying out this process, cultivation occurs in an aqueous medium. In carrying out this submerged cultivation, any conditions that are conventionally utilized in carrying out submerged cultivation may be used. In the preferred process, the fermentation is carried out at a temperature between 10° and 35° C., at a pH range of about 6.5 to about 8.0, and for about 24 to about 72 hours. The preferred conditions for the cultivation process, using the nutrient media of the present invention, are a temperature between about 22° C. and about 30° C., a pH of about 7.2, and a cultivation period of about 30–36 hours.

The pH of the culture medium is adjusted between 6.5 and 8.0, preferably between 7.0 and 7.5. The adjustment of pH may be effected with substances including but not limited to aqueous solutions of sodium hydroxide, potassium hydroxide or ammonium hydroxide. These substances are well-known to practitioners in the art.

In the process of this invention, formation of pigment increases in proportion to the growth of the culture, with the maximum pigment formation being obtained in about 30–36 hours.

After the culture time is completed, the zeaxanthin content of the fermentation medium can be determined. For this purpose, the biomass is separated from the nutrient substrate by centrifugation and the zeaxanthin is extracted from the cells. The zeaxanthin content of the extraction solution can be determined colorimetrically by comparison with standard solutions of synthetic zeaxanthin in the same solvent.

At the end of culture, the fermentation broth may be concentrated and the zeaxanthin extracted from the cells, using a polar organic solvent, including but not limited to acetone, hexane, or a chlorinated solvent, such as chloroform, or by supercritical fluid extraction. See, for example, F. Favati, et al., *J. Food Sci.* 53(5): 1532–1535 (1988).

Alternatively, the biomass may be separated from the culture medium, for example by centifugation, decantation or filtration. If centifugation is used, cell recovery may be improved by the addition of bentonite and calcium chloride (see Example 2). In the preferred method, bentonite and calcium chloride are added to the fermentation broth, which is then heated in order to kill any viable cells. The broth is then centrifuged in order to recover a paste of packed cells and unused media solids. The cell paste may be slurried in water to a workable viscosity. EDTA (about 0.2%), BHA (about 0.05%), Tween (about 0.1%), and tocopherol acetate (about 0.15%) may be added to the slurry in order to prevent or reduce pigment breakdown; the percent used is based on cell weight in the slurry. The slurry is then homogenized (using, for example, glass bead cell rupture or a high pressure homogenizer) and dried for future use. The preferred method of drying is by spray-drying.

The biomass may be used as an additive in chicken feeds, for example, or it may be extracted with a polar organic solvent, as noted above.

The pigment-containing biomass can be advantageously utilized in accordance with this invention to color foodstuffs without the necessity for isolating pure zeaxanthin pigment. On the other hand, the intracellular zeaxanthin can be separated from the cells in a conventional manner. A preferred method of separating or extracting the zeaxanthin involves carefully drying the cell mass; pulverizing the dried cell mass; digesting the pulverized material with an inert organic solvent; filtering the solution; and isolating the pure zeaxanthin by elution of the filtration residue with an inert organic solvent. The individual steps of the preferred method can be carried out in a conventional manner. According to a particularly preferred method of separating the zeaxanthin, the cell-mass is dried by spray drying. Inert organic solvents include but are not limited to a lower alkanol, preferably ethanol; a ketone, preferably acetone; or a halogenated hydrocarbon, preferably chloroform. Further, particularly preferred is to take up the evaporation residue in ethyl acetate, a lower alkanol or mixtures thereof. Further, particularly preferred is filtering the solution over silica gel, neutral aluminum oxide, or magnesium silicate. Still more preferred is eluting the zeaxanthin with a chlorinated hydrocarbon, particularly methylene chloride or dichloroethylene or a dilower alkyl ether, particularly diethyl ether. Alternatively, the dried powder may be extracted using supercritical extraction with $CO_2$ gas under high pressure.

The pigment formed by Flavobacterium consists of up to 95-99 percent of zeaxanthin. Tests show that Flavobacterium-produced zeaxanthin is identical to zeaxanthin isolated from Zea mays.

The almost pigment-free cell mass remaining after extraction of the zeaxanthin can be used as an ideal source of proteins (essential amino acids, such as methionine and lysine) and vitamins (especially vitamins of the B group and, particularly, vitamin $B_{12}$) for the raising of poultry.

The present invention also includes mutants and variants of *F. multivorum* having substantially the same taxonomic characteristics as the AFB-44, ATCC 55238, strain shown in Example 4. Mutations may be induced by conventional techniques, as noted above.

All publications mentioned in this specification are indicative of the level of skill of those skilled in the art to which this invention pertains. All publications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

Example 1. Isolation of *F. multivorum*

Samples from the environment were screened for yellow-orange pigmented bacteria by streaking the samples directly onto an agar media petri plate (2.0% agar, 0.02% trypticase soy broth, 0.02% yeast extract and 0.25% sodium chloride). In addition, samples were incubated with illumination in water-filled whirl-pack bags for 3 days at room temperature as an enrichment procedure (with 0.5% sodium chloride) prior to streaking on agar. Pigmented strains from a number of culture collections from around the world were maintained on trypticase soy agar+1% yeast extract slants. The described *F. multivorum* strain AFB-44 was isolated from a fresh water spring near High Ridge, Mo.

Hundreds of strains isolated in this manner or obtained from culture collections were then inoculated into a pigment screening broth (autoclaved at 121° C.; 30 minutes):

| | |
|---|---|
| Trypticase soy broth | 1.0% |
| Pyridoxine | 0.001% |
| Casitone | 0.25% |
| Disodium phosphate | 1.0% |
| Sodium caseinate | 0.25% |
| Yeast extract | 0.25% |
| Corn steep liquor | 0.1% |
| Methionine | 0.1% |
| Ferrous sulfate | 0.01% |
| $MG^{++}$ sulfate | 0.01% |
| $MN^{++}$ sulfate | 0.01% |
| $Zn^{++}$ sulfate | 0.01% |
| Thiamine | 0.01% |
| Glycerol | 0.5% |
| pH | 7.8 |

Cultures were incubated at 25° C. (with illumination) for 72 hours or until sufficient growth occurred, and were harvested by pelleting with centrifugation (25,000 rcf). They were grown as 50 ml batches in 300 ml dimpled flask at 250 rpm on a gyratory incubator/shaker. Pellets were frozen and then extracted with acetone. Centrifuged extracts were then dried and brought up in hexane and applied to an alumina chromatography apparatus and developed per the AOAC method for xanthophylls [Quackenbush et al, *J. Assoc, Off. Anal. Chem.* 56: 748-753 (1973)]. Various fractions were collected, particularly dihydroxycarotenoids, and were scanned for absorption maxima by a Beckman scanning spectrophotometer.

Out of thousands of starting isolates, 12 isolates produced a similar absorption spectra and chromatographic retention to that reported for zeaxanthin. These isolates were then grown, extracted and submitted for authentication to an outside expert by reverse-phase HPLC [Quackenbush F., *J. Liq. Chrom.* 10(4): 643-653 (1988)]. One culture produced a relatively pure yield of zeaxanthin as its major pigment (95%).

This culture was submitted in confidence to two independent laboratories for a taxonomic work-up. Both laboratories concluded that the culture was not similar to previously described zeaxanthin-producing bacteria. The culture strain was characterized as a *Flavobacterium multivorum* strain. This was the first report of zeaxanthin production by this species.

Example 2. Cultivation of *Flavobacterium multivorum*

The culture is maintained on a slant tube of Plate Count Agar. These slants are inoculated and then incubated for 24 hours at 30° C. Stock slants are stored in a refrigerator for use as inoculum for liquid media.

The liquid medium has the following composition:

| | |
|---|---|
| Corn Steep liquor | 7.0% |
| Corn Flour | 5.0% |
| $FeSO_4$ | .001% |
| Soapstock | 1.0% |
| Yeast Extract | .05% |
| $Na_2HPO_4$ | .1% |
| Termamyl 120L | .01% |
| Water | 86.839% |
| | 100.00% |

The nutrient medium was adjusted to a pH of 7.6 using concentrated (10N) sodium hydroxide. The medium was then heated to about 85° C. and held for 30 minutes; this allowed enzymatic hydrolysis of the starch into a dextrin. The heated medium was then sterilized at 121° C. for 30 minutes. After cooling, the medium was inoculated from a stock slant (as prepared above), or from a previously inoculated broth culture, which was about 24 hours old. The level of inoculum was about 5% V/V.

The growth conditions for the inoculated nutrient medium were 30° C.; pH 7.2 36 hours; 5% inoculum by weight; and continuous aeration. Aeration was 200 RPM in a shaker incubator using 300 ml dimpled erlenmeyer flasks with 30 ml of medium, or, in a fermentor stirring at 400 PRM, bubbling air at a rate sufficient to maintain a dissolved oxygen level of 50% saturation. In this experiment, the bubbling rate was about 0.25 VVM.

At approximately 12 hours into the fermentation, lipase and glucoamylase were added (at low levels, about 0.03% by weight of the medium, or 30 lipase units and 6 AG units per liter of fermentation medium).

After completion of fermentation, *Flavobacterium multivorum* cells were harvested from the medium by centrifugation after the addition of 0.006 g/l to 0.01 g/l bentonite and 0.16 g/l to 0.4 g/l $Cacl_2$. The medium was then heated to 50° C. in order to kill any viable cells, then the broth was centrifuged in order to recover a thick paste of packed cells and unused medium solids. The cell paste was then reslurried, and EDTA (0.2%), tocopherol acetate (0.015%), BHA (0.05%), and Tween 80 (0.1%) were added to the slurry. The slurry was then homogenized and dried for future use. This dried product was then used for the layer and broiler feeding studies. The dried biomass was stored for two months at room temperature to simulate a storage stability test.

Example 3

The following experiment was done to demonstrate the advantages of the described process versus growth on other media described in the literature and patents.

Media with the following compositions were formulated, autoclaved, cooled and inoculated with a strain of *F. multivorum,* as noted.

Media A, B, and C are media described in the patents noted in the Relevant Literature section. Media D, E and F are nutrient media of the present invention.

| | A (%) | B | C | D | E | F |
|---|---|---|---|---|---|---|
| Glucose* | 0.5 | 3% | 10% | — | — | — |
| Tryptone | 1.0 | 1.0 | 1.25% | — | — | — |
| Yeast Extract | 1.0 | 1.0 | 2.1% | 0.1 | 0.1 | 0.1 |
| NaCl | 1.0 | — | — | 0.5 | 0.5 | 0.5 |
| $MgSO_4$ | 0.5 | 0.5% | 0.5% | 0.1 | 0.1 | 0.1 |
| Corn Steep Liquor | — | — | 1.85 | 4% | 8.0 | 8.0 |
| Corn Flour | — | — | — | 3% | 5.0 | 5.0 |
| Vegtable Oil | — | — | 0.08 | 1.0% | 1.0 | **** |
| Na Acetate | — | — | — | — | 0.1 | 0.1 |
| $NH_4SO_4$ | — | — | — | — | 0.5 | 0.5 |
| Thiamine | — | — | — | 0.05 | 0.05% | 0.05% |
| Amylase** | — | — | — | 0.1 ml/l | 0.1 ml/l | 0.1 ml/l |
| Glucoamylase | — | — | — | — | 0.05 ml/l | 0.05 ml/l |
| Lipase*** | — | — | — | — | 0.05 ml/l | 0.05 ml/l |
| $FeSO_4$ | — | — | — | 0.001 | 0.001 | 0.001 |

*Glucose sterilized separately
**Amylase was Termamyl (120L, Novo, Inc.)
***Lipase was Palatase (A 750L, Novo, Inc.) filter-sterilized and added at 12 hrs. Glucoamylase was (AMG 200L, Novo, Inc.) filter-sterilized and added at 12 hrs.
****Corn oil soapstock substituted for vegetable oil on equal weight basis.

All pH's were adjusted to 7.5 and maintained by periodic checking. Only medium C required significant adjustments. All media were autoclaved at 121° C. for 30 minutes except D and E, which additionally were held at 80°-90° C. for 30 minutes just prior to sterilization. All media except were inoculated at 5% volume/-volume with the AFB-44, ATCC 55238, strain and incubated on a rotary shaker at 250 rpm for 24 hours at 30° C. and then 24 hours at 26° C. prior to centrifugal harvesting. Media E (with mutant) & F were inoculated separately with a mutant derived from the AFB-44, HTCC 55238, strain and, in this case, the mutant grown in media E & F was incubated at 30° C. for just 32 hours. The results are shown in the following table.

| | Results | | | | | | |
|---|---|---|---|---|---|---|---|
| | A | B | C | D | E | E (with mutant) | F |
| Cell yield gms/liter | 5.5 | 4.6 | 12.8 | 32 | 44 | 45 | N.D. |
| True cell yield gms/liter | N.D.* | N.D. | 11 | 24 | 32 | 36 | N.D. |
| Zeaxanthin yield ug/ml | 6 | 9 | 6.5 | 36 | 31 | 512 | 512 |

*N.D. = not determined

Cell yields were calculated by centrifuging at 20,000 rcf for 10 minutes, decanting the supernatant, and drying the resulting pellet at 105° C. for 24 hours. True cell yields were calculated by first centrifuging at 3,000 rcf to remove fermentation insolubles, and drying the pellet; the dry weight of the pellet was subtracted from the regular cell yield values. Zeaxanthin was calculated by extracting the frozen cell pellets with acetone and then reading the $O.D._{450}$ on a spectrophotometer of the centrifuged extracts. These readings were then multiplied by appropriate factors for extinction coefficient and dilution effects.

Additionally, medium D was used to culture other *Flavobacterium multivorum* strains in order to show that the nutrient medium of the present invention works with other *F. multivorum* strains, and to show that the nutrient medium leads to improved zeaxanthin yield.

Medium D was inoculated with strains K2361 or K1180 (described in Example 4), and cultivated as shown in Example 2. K2361 produced a crude cell yield of 25 g/l, a true cell yield of 13 g/l, and 11 μ/ml zeaxanthin. K1180 produced a crude cell yield of 24.5 g/l, a true cell yield of 12.5 g/l, and 4 μ/ml zeaxanthin. The results for K2361 show that the nutrient medium of the present invention improves the cell yield and amount of zeaxanthin produced by some strains of *F. multivorum.* The results for K1180 show that the more economical nutrient medium of the present invention produces about the same cell yield and amount of zeaxanthin as more expensive nutrient media.

The results of these experiments demonstrate that with the AFB-44 strain of *F. multivorum* that:

a) media D&E (the present invention) produce significantly greater cell yields and zeaxanthin yields than the media A, B and C described in previous patent literature;

b) although media D and E have approximately equal solids initially, medium E provides a better yield of cells and pigment;

c) while media A, B and C are very expensive relative to D and E, the latter produced better yields;

d) by using mutants of the AFB-44, ATCC 55238, strain adapted to medium E, very high cell and pigment yields could be demonstrated in production times as low as 32 hours (i.e., more rapid growth). AFB-44, ATCC 55238, medium mutants in E resulted in the highest cell and pigment yields yet established.

e) soapstock can be substituted for vegetable oil, while retaining equal zeaxanthin yield.

Example 4. Comparison to Other Flavobacterium Microorganisms

An isolate of *Flavobacterium multivorum* (AFB-44, ATCC 55238) was compared taxonomically to other Flavobacterium species: ATCC 21588 (or 21588L) and ATCC 11947 are described in U.S. Pat. Nos. 3,841,967; 3,951,742; and 3,951,743. ATCC 21081 is disclosed in U.S. Pat. Nos. 3,891,504 and 3,841,967. It should be noted that the patent strains, ATCC 21588 and 21081, would not be classified in the Flavobacterium genus according to the new taxonomic scheme described in the 1984 edition of Bergey's Manual.

ATCC No. 21081 is significantly different from the AFB-44, ATCC55238, strain in its growth temperature requirements and its absolute requirement for salt.

ATCC No. 21588 is significantly different from *F. multivorum* in many fermentation and utilization patterns; it is significantly different in that *F. multivorum* strains grow well at 35° C. and in motility-nitrate agar and infusion broth, while ATCC 21588 does not. In addition, ATCC 21588 is sensitive to penicillin and vancomycin, while *F. multivorum* is not. ATCC 21588 was also LANA (2-alanint-4-nitroanilide) negative and could produce spore like structures; both attributes are uncharacteristic of the Flavobacterium genus.

The taxonomy work was carried out by a recognized expert in pigmented bacteria taxonomy. His conclusion that the *F. multivorum* strain is significantly different from ATCC 11947, 21081, and 21588 was supported by a similar conclusion from the microbial taxonomy service of the American Type Culture Collection.

| Acid from | No. 21588 | No. AFB-44, ATCC 55238 |
|---|---|---|
| adonitol | − | − |
| L-arabinose | + | + |
| cellobiose | + | + |
| ethanol | − | − |
| fructose | + | + |
| galactose | + | + |
| glucose | + | + |
| inositol | + | − |
| lactose | + | + |
| maltose | + | + |
| mannitol | + | − |
| melibiose | N.D.* | N.D. |
| raffinose | + | + |
| rhamnose | − | +w** |
| sorbital | − | − |
| sucrose | + | + |
| xylose | − | + |
| D-arabinose | − | + |
| salicin | − | + |
| trehalose | + | + |

*N.D. = not determined
**w = weak and/or delayed

| Alkali from | No. 21588 | No. AFB-44, ATCC 552/38, |
|---|---|---|
| acetamide | − | − |
| β-alanine | + | − |
| allantoin | + | + |
| arginine | − | − |
| azelate | − | − |
| citrate | + | − |
| gelatin | − | − |
| gluconate | + | − |
| glycolate | + | − |
| histidine | − | + |
| itaconate | − | − |
| malonate | + | − |
| nicotinamide | − | − |
| oxalate | − | − |
| saccharate | + | − |
| tartrate | + | − |
| urea | + | + |
| catalase | + | + |
| Fluorescence | − | − |
| Growth at 42° C. | − | − |
| on cetrimide | − | − |
| on Mac agar* | − | − |
| on MBMM-Ac** | + | − |

*Mac agar = MacComkey agar

| Hydrolysis of | No. 21588 | No. AFB-44, ATCC 552/38, |
|---|---|---|
| Casein | − | − |
| DNA | − | −w* |
| Esculin | +w | + |
| Gelatin | − | − |
| Starch, Argo | − | − |
| Tween 80 | − | + |
| Indole | − | − |
| KOH test** | ?− | + |
| LANA*** | − | + |
| Lysine (LDC) | − | − |
| Motility | − | − |
| Nitrate - gas | − | − |
| - nitrate | − | − |
| Zn test | + | + |
| Nitrate - gas | − | − |
| Ornithine (ODC) | − | − |
| Oxidase | + | + |
| Phenylalanine (PPA) | − | − |

*w = weak and/or delayed
**KOH test = potassium hydroxide test
***LAHA test = 2-alanine-4-nitroanidide

| Sensitive to | No. 21588 | No. AFB-44, ATCC 552/38, |
|---|---|---|
| penicillin (2 U) | + | − |
| polymyxin B (300 U) | + | − |
| vancomycin (5 μg) | + | − |

| Growth on: | ATCC #21081 | AFB-44, ATCC 552/38, |
|---|---|---|
| TSA,* RT** | nil | good |
| TSA, 30° C. | nil | good |
| PYEPO, RT | good | nil |
| PYEPO,*** 30° C. | nil | nil |

*TSA = Trypticase Soy agar
***RT = Room temperature

ATCC #21081 is a gram-negative rod, and nonmotile in a wet mount. Its growth characteristics are not those of genus *Flavobacterium* as presently defined by Holmes et al. in Bergey's Manual (1984), but are compatible with some taxonomy of Weeks' Flavobacterium, Section II in Bergey's Manual (1984). It has an obligate requirement for NaCl and cannot grow at 30° C.

Example 5—Comparison of F. multivorum Strains

The original AFB-44, ATCC 55238, strain, after isolation as previously described, was identified as a zeaxanthin-producing bacterium. After initial comparisons with known Flavobacterium strains, it was determined that it was uniquely different and that it should be categorized as *F. multivorum*. During the initial extensive screening procedure, this was the only Flavobacterium strain that could be identified to produce zeaxanthin. This included the entire collections of the *Flavobacterium/Cytophaga* group from five public collections from around the world. It was concluded that zeaxanthin-producing, pigmented bacteria were very rare. After identification of the organism, it was determined that additional *F. multivorum* strains should be checked. *F. multivorum* strains available from the UCLA-Microbiology Department collection, Nos. K-1213, K-1204, K-1180, K-2361, and K-2303, were compared with strain AFB-44, ATCC 55238, as follows. The strains were grown on PCA slants and inoculated into a liquid medium and grown at 30° C. for 24 hours and 24° C. for 48 hours in dimpled flasks on a reciprocal shaker prior to harvesting by centrifugation. In this experiment, illumination was also used. Samples were extracted with acetone from the frozen pellets and the extracts were dried under $N_2$ gas, brought back up in hexane, and applied to an alumina (neutral) column chromatography apparatus. Increasing acetone/hexane ratios were used to fractionate; spectrophotometric scans were used to check absorption maxima of each fraction. The following results were obtained.

| Medium | | | |
|---|---|---|---|
| Glucose | 1.0% | $K_2HPO_4$ | 0.5% |
| Tryptone | 1.0% | NaCl | 0.25% |
| Yeast Extract | 1.0% | Thiamine | 0.01% |
| $MgSO_4$ | 0.5% | pH | 7.5 |

| Pigments | Hydrocarbon fraction | Mono-Hydroxy carotenoids | Dihydroxy carotenoids | Absorption maxima of extracts |
|---|---|---|---|---|
| K-1180 | +5.3 | + | + | + | 427, 451, 477 |
| K-1204 | +4.9 | + | + | + | 425, 452, 480 |
| K-1213 | +2.8 | + | + | + | 427, 452, 482 |
| K-2303 | v.sl.+ | nd** | nd | nd | nd  nd  nd |
| K-2361 | +6.1 | ++ | + | + | 430, 452, 477 |
| AFB-44, ATCC 552/38, | +16 μg | + | + | ++ zeaxanthin | 430, 452, 477<br>429, 452, 477 |

*v. sl. = very slight
**nd = not determined

The data demonstrated that:
a) other strains of *F. multivorum*, surprisingly, produce zeaxanthin;

b) it appears that every strain of *F. multivorum* produces a quantifiable amount of pigment (however, in this experiment, K-2303 could not be shown to produce quantifiable pigment, i.e., is a weak pigmenter, and the production of zeaxanthin could not be determined);

c) the wild strain of AFB-44, ATCC 55238, produces more pigment and a better zeaxanthin/total carotenoids ratio than the other strains;

d) column chromatography shows that the dihydroxy carotenoid produced by all of the strains (except K-2303) appears to be primarily zeaxanthin;

e) that publicly available *F. multivorum* strains produce zeaxanthin; and f) that a heretofore unknown grouping of Flavobacterium share a propensity towards zeaxanthin as a common pigment of their cell composition.

Example 6

Feeding studies demonstrating increased biological availability, stability and pigmenting power of a biomass composition relative to current commercial processed pigment sources.

A biomass composition, which had been prepared as shown in example 2 and had been stored at room temperature for two months, was fed to broiler chickens and compared to stabilized and saponified extracts of marigold flowers. The basal diet was as follows:

| Ingredient | Starter | Grower (Wheat) |
|---|---|---|
| Wheat | 45.32 | 61.46 |
| Corn | 10.00 | 10.00 |
| Soybean Meal | 31.35 | 14.32 |
| Poultry Meal | 2.40 | 6.00 |
| Poultry Fat | 7.28 | 5.31 |
| Limestone | 1.24 | 1.03 |
| Decal. Phos.* | 1.44 | .96 |
| Salt | .40 | .30 |
| Choline | .20 | .20 |
| Trace Mineral | .10 | .10 |
| Vitamin Premix | .05 | .05 |
| Lysine | — | .12 |
| DL-Methionine | .18 | .10 |

-continued

| Ingredient | Starter | Grower (Wheat) |
|---|---|---|
| Coccidiostat | .05 | .05 |
| Nutrients | | |
| Protein, % | 23.00 | 19.00 |
| Energy (Kcal/lb) | 1450 | 1450 |
| Calcium, % | 1.00 | .90 |
| Total Phos., %** | .70 | .65 |
| TSAA, %*** | .93 | .75 |
| Lysine, % | 1.26 | 1.00 |

*Decal. Phos. = decalcified phosphate
**Total Phos. = total phos.
***TSAA = total soluble amine acids

| RESULTS: | 6 weeks color score* | 6 week average live weight (grams) | 6 week feed conversion |
|---|---|---|---|
| Control (no added pigment) | 2.0 | 1591 | 1.85 |
| 25 ppm xanthophyll from Marigold extract | 6.7 | 1549 | 1.90 |
| 10 ppm zeaxanthin added from Biomass composition | 7.1 | 1541 | 1.87 |
| 25 ppm zeaxanthin Biomass composition | 9.3 | 1550 | 1.84 |

*Scored by 5 Judges subjectively using the Roche color fan (shank color scores).
**Similar results (potency) were demonstrated with two other leading marigold extracts.

The results show no deleterious effects on the chickens and that 10 ppm of zeaxanthin from the biomass composition was biologically available and equal to 25 ppm of xanthophyll from marigold extract, the best natural stabilized and processed commercial natural source of xanthophylls. The xanthophyll must be biologically available to show improved pigmentation and also appears to pigment more readily. The results demonstrate a microbial pigment composition that surprisingly has good stability and biological availability without the need for expensive extraction and saponification processes. In addition, no harmful effects can be seen in the growth data.

I claim:

1. A process for the production of zeaxanthin comprising:

culturing a strain of pigmented *Flavobacterium multivorum* in a nutrient medium that comprises at least one assimilable carbon source, and at least one assimilable nitrogen source, and recovering zeaxanthin from the culture.

2. The process according to claim 1, wherein said *Flavobacterium multivorum* is strain ATCC 55238, or a mutant thereof that is capable of producing zeaxanthin.

3. The process according to claim 1, wherein said nutrient medium contains an enzyme-treated carbon source and a corn step liquor nitrogen source.

4. The process according to claim 3, wherein said enzyme-treated carbon source is treated with α-amylase.

5. The process according to claim 1, wherein said assimilable carbon source is selected from the group consisting of corn, rice, milo, wheat, flours derived from said grains, starches derived from said grains, malto-dextrin and glucose.

6. The process according to claim 5, wherein the glucose level in said medium is less than about 0.035% by weight.

7. The process according to claim 1, wherein said assimilable nitrogen source is selected from the group consisting of corn steep liquor, hydrolyzed soybeans, ammonium phosphate, ammonium sulfate, ammonia, yeast extract, and a hydrolysate of a Flavobacterium biomass.

8. The process according to claim 1, wherein the nutrient medium further comprises mineral salts, a fat source and growth factors.

9. The process according to claim 1, wherein said culturing is conducted in a temperature range of about 16° C. to about 38° C., at a pH range of about 6.0 to about 8.5, and for about 24 to about 72 hours.

10. The process according to claim 9, wherein said culturing is conducted in a temperature range of about 22° C. to about 34° C.

11. The process according to claim 9, wherein said culturing is conducted at a pH of about 6.5 to about 8.0.

12. The process according to claim 9, wherein said culturing is conducted for about 32 hours.

13. The process according to claim 2, wherein said nutrient medium contains an enzyme.

14. The process according to claim 13, wherein said enzyme is selected from the group consisting of glucoamylase, lipase, or mixtures thereof.

15. The process according to claim 1, wherein the zeaxanthin is recovered from the culture by extraction with an inert organic solvent and removal of the solvent from the zeaxanthin.

16. The process according to claim 15, wherein the solvent is removed form the zeaxanthin by evaporation.

17. The process according to claim 1, wherein the zeaxanthin is recovered from the culture as a cell paste.

18. The process according to claim 17, wherein the cell paste is slurried in an emulsifier, homogenized and dried.

19. A process for the preparation of zeaxanthin comprising:

culturing a strain of *Flavobacterium multivorum* in a medium comprising about 4.0% to about 8.0% corn steep liquor, about 3.0% to about 5.0% corn flour, about 1.0% fat and about 0.1 ml/l amylase, and recovering the zeaxanthin therefrom.

* * * * *